April 18, 1950 F. MEILLAND Plant Pat. 933
ROSE PLANT
Filed Oct. 6, 1948
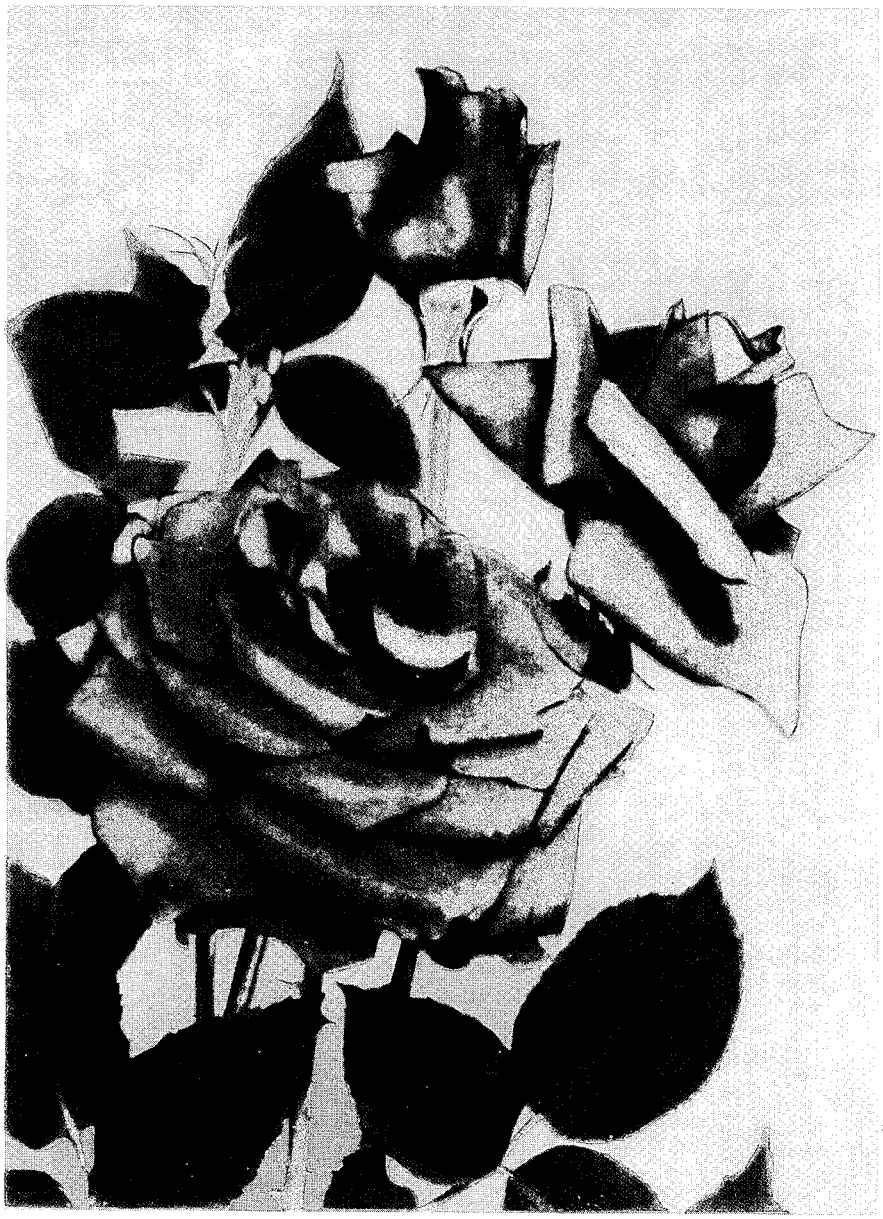
Inventor
F. Meilland
By Robb & Robb
Attorneys Patented Apr. 18, 1950

Plant Pat. 933

UNITED STATES PATENT OFFICE

933

ROSE PLANT

Francis Meilland, Cap Azura, Cap D'Antibes, France, assignor to The Conard-Pyle Company, West Grove, Pa., a corporation of Pennsylvania Application October 6, 1948, Serial No. 53,011

1 Claim. (Cl. 47—61)

The present invention relates to a new and distinct variety of rose plant having outstanding qualities and characteristics among which are the dominating rich depth of coloring in near-dark shades of red and the intensity of volume of fragrance surpassed by no other hybrid tea rose of which I am aware.

Asexual reproduction shows that these characteristics hold true through succeeding propagations.

In the drawing are shown specimens of this new variety, illustrating the flowers at different stages of development from bud to full blown blossoms.

The following is a detailed description of the new variety, all reference to color being in accordance with Ridgway's Color Standards and Nomenclature and ordinary dictionary definition.

Type: Hardy; bush; outdoor; for cut flowers and garden decoration; seedling.
Class: Hybrid tea.
Propagation: Holds its distinguishing characteristics through succeeding propagations by budding.
Parentage: (Rome Glory × Congo) × Eassin.

*Flower*

Locality where grown: West Grove, Pennsylvania.
Flowers borne: Singly to stem; on normal or strong long stems.
Quantity of bloom: Free; outdoors.
Continuity: Continuous.
Fragrance: Penetrating; tea.
Bud:
*Peduncle.*—Long; medium heavy; erect; medium rough; few brown prickles and occasionally thorns. Color—Parrot Green, Plate VI.
*Before calyx breaks.*—Size—small. Form—pointed; ovoid; with foliaceous appendages on the surface of the bud; with slender and stout foliaceous parts extending beyond the tip of the bud equal to or more than its length, some slender, some very large and almost leaf-like.
*As calyx breaks.* — Color — Pomegranate Purple, Plate XII, occasionally with streaks of Victoria Lake, Plate I.
*As first petal opens.*—Size—large. Form—ovoid to globular. Color—outside: Oxblood Red, Plate I; inside—Carmine, Plate I, shading to velvety Victoria Lake Plate I.
*Opening.*—Opens up well.

Bloom:
*Petalage.*—Double; from 35 to 40 petals; arranged irregularly.
*Form.*—Full high center at first; remaining high centered; petals remaining at first loosely rolled outward; becoming later, at maturity, very tightly rolled outward.
Petals: Thick; leathery soft; with inside velvety and outside leathery.
*Shape.* — Outside—round. Intermediate—obovate. Inside—obovate.
*Color.*—Colors may be modified by being shaded with other colors. Occasionally there is a light, almost white, streak down the center of the petal. This occurs more frequently down the outer surface.

This description of a newly opened flower was made from a rose grown outdoors in the month of August at West Grove, Pennsylvania:

*Color.* — *Outside petal* — outside surface: Pomegranate Purple, Plate XII; inside surface: velvety Carmine, Plate I. *Intermediate petal*—outside surface: Nopal Red, Plate I; inside surface: velvety Carmine, Plate I. *Inner petal*—outside surface: Nopal Red, Plate I; inside surface: velvety Carmine, Plate I.

This description was made from a rose that was open for three days in the month of August at West Grove, Pennsylvania:

*Color.*—*Outside petal* (the following colors are usually modified by blackish shadings)—Outside surface: dark Rose, Plate XII; inside surface: Picric Yellow, Plate IV, at the base, shading to Tyrian Rose, Plate XII, to Carmine, Plate I, and to velvety Victoria Lake, Plate I.
*Inside petal* (the following colors are frequently darkened by blackish shadings)—outside surface: Rose Red, Plate XII, occasionally with Rose Pink, Plate XII, area down center; inside surface: Picric Yellow, Plate IV, at the base, shading to Rose color, Plate XII, to Carmine, Plate I, slightly covered with velvety Victoria Lake, Plate I.
*General color effect.*—Newly opened flower—velvety Carmine, Plate I, with blackish shadings. Three days open—dark velvety Carmine, Plate I, to bright velvety Carmine, Plate I, with blackish shadings.
*Behavior.*—Drop off cleanly.
*Flower longevity.*—Cut roses grown outdoors, kept at living room temperatures 4 to 5 days in August.

*Reproductive organs*

Stamens: Medium number; arranged regularly about pistils.
Filaments: Medium length; most with anthers. Color—Rose color, Plate XII.
Anthers: Medium size; all open at once; a few anthers fused with petaloids. Color—Zinc Orange, Plate XV.
Pollen: Moderate amount. Color—Light Cadmium, Plate IV.
Pistils: Medium number.
Styles: Uneven; medium length; thin; bunched.
Stigma: Salmon Buff, Plate XIV.
Ovaries: All enclosed in calyx.
Hips: Globular; walls thick. Color—Light Dull Green Yellow, Plate XVII, to Lettuce Green, Plate V.
Sepals: Permanent; long; recurved.
Seeds: Many; large.

*Plant*

Foliage:
*Leaves.*—Compound of three or five leaflets; normal amount; medium size; leathery.
*Leaflets.*—Shape—oval with apex acute. Base—round. Margin—simply serrate.
*Color.*—*Mature*—upper surface: Calla Green, Plate V; under surface: Vetiver Green, Plate XLVII, with slight reddish tinges. *Young*—upper surface: Claret Brown, Plate I, with light Yellow Green, Plate VI, areas along midrib; under surface: Claret Brown, Plate I.
*Rachis.*—Medium heavy. Upper side: grooved; hairy; under side: sparsely thorny.

*Stipules.*—Medium length; medium width; with medium length points turning out at an angle of less than 90°.
*Disease.*—Resistant to mildew and blackspot.
Growth:
*Habit.*—Upright; well branched.
*Growth.*—Free; vigorous.
*Canes.*—Heavy.
*Main stems.*—Gray-green. *Thorns*—many; medium length; slightly hooked downward; with long, narrow base. *Prickles*—several with yellowish, reddish-brown base. *Hairs*—none.
*Branches.*—Grey-green. *Thorns*—many; medium length; slightly hooked downward; with medium length narrow base. *Prickles*—several; yellowish with brownish tips. *Hairs*—none.
*New Shoots.*—Rainette Green, Plate XXXI, with Acajou Red, Plate XIII, tinges. *Thorns*—many; medium length; slightly hooked downward, with narrow base. *Prickles*—several; reddish. *Hairs*—none.

I claim:
A new and distinct variety of rose plant characterized as to novelty especially by the dominating dark red coloring of the flowers and intensity and volume of fragrance thereof, substantially as shown and described.

FRANCIS MEILLAND.

No references cited.